(12) United States Patent
Takeuchi et al.

(10) Patent No.: US 12,025,608 B2
(45) Date of Patent: Jul. 2, 2024

(54) ESTIMATION METHOD, ESTIMATION DEVICE, AND PROGRAM

(71) Applicant: NIPPON TELEGRAPH AND TELEPHONE CORPORATION, Tokyo (JP)

(72) Inventors: Yosuke Takeuchi, Tokyo (JP); Yosuke Okamura, Tokyo (JP); Junichiro Tamamatsu, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 17/776,265

(22) PCT Filed: Nov. 13, 2019

(86) PCT No.: PCT/JP2019/044556
§ 371 (c)(1),
(2) Date: May 12, 2022

(87) PCT Pub. No.: WO2021/095166
PCT Pub. Date: May 20, 2021

(65) Prior Publication Data
US 2022/0390430 A1    Dec. 8, 2022

(51) Int. Cl.
*G01N 33/38*    (2006.01)
*G01M 5/00*    (2006.01)
*G01M 99/00*    (2011.01)

(52) U.S. Cl.
CPC ........ *G01N 33/383* (2013.01); *G01M 5/0033* (2013.01); *G01M 5/0058* (2013.01); *G01M 99/007* (2013.01)

(58) Field of Classification Search
None
See application file for complete search history.

(56) References Cited

U.S. PATENT DOCUMENTS

| 11,585,721 B2* | 2/2023 | Ohta ................. G06T 7/0002 |
| 2004/0101365 A1* | 5/2004 | Larsen ................ E01C 7/32 |
| | | 404/70 |

FOREIGN PATENT DOCUMENTS

| CN | 102013150 A | * 4/2011 | |
| CN | 109827855 A | * 5/2019 | .......... G01N 17/006 |
| (Continued) | | | |

OTHER PUBLICATIONS

Kaneko et al. (2011) "Crack inspection technology for concrete structures using digital camera images" NTT Technical Journal, vol. 23, No. 12, pp. 21-24.

(Continued)

*Primary Examiner* — Giovanni Astacio-Oquendo
*Assistant Examiner* — Carl F. R. Tchatchouang

(57) ABSTRACT

An estimation method includes: an acquisition step (S101) of acquiring deflection stress information that indicates a relationship between a deflection and a tensile stress of a specimen (200) of a reinforced concrete structure; and a derivation step (S102) of deriving an estimation formula for estimating a depth of a crack generated in the reinforced concrete structure when a deflection of the reinforced concrete structure is no less than a first deflection of the specimen at a start of a generation of the crack, and is no greater than a second deflection of the specimen at an end of the generation of the crack.

20 Claims, 4 Drawing Sheets

(56) References Cited

FOREIGN PATENT DOCUMENTS

KR         20110094619 A  *  8/2011
WO     WO-2019242366 A1 * 12/2019  ........... G01N 33/383

OTHER PUBLICATIONS

Kiyoharu Sasaki (2017) "Technological development to innovate the operation of access facilities" NTT Technical Journal, vol. 29, No. 2, pp. 51-55.

* cited by examiner

ESTIMATION METHOD, ESTIMATION DEVICE, AND PROGRAM

CROSS-REFERENCE TO RELATED APPLICATIONS

This application is a U.S. National Stage Application filed under 35 U.S.C. § 371 claiming priority to International Patent Application No. PCT/JP2019/044556, filed on 13 Nov. 2019, the disclosure of which is hereby incorporated herein by reference in its entirety.

TECHNICAL FIELD

The present invention relates to an estimation method, an estimation device, and a program.

BACKGROUND ART

Reinforced concrete structures are composite structures in which concrete protects the reinforcing steel bars from corroding. Concrete is alkaline, and therefore the reinforcing steel bars of healthy reinforced concrete structures do not corrode. However, if cracks are generated in a reinforced concrete structure, the neutralization of the concrete and the corrosion of the reinforcing steel bars develop from the cracked portion, and the strength of the reinforced concrete structure decreases. Therefore, whether or not cracks have occurred in a reinforced concrete structure and whether or not the cracks generated in the reinforced concrete structure have reached a reinforcing steel bar can be important criteria for evaluating the health of the reinforced concrete structure.

Currently, visual inspection is the mainstream of crack detection for reinforced concrete structures. However, detection technologies that employ image analysis have also been developed. For example, NPL 1 discloses a technology for detecting minute cracks in a concrete pillar by analyzing an image of the concrete pillar taken remotely using a digital camera. For example, NPL 2 discloses a technology for quantitative and area-wise detection of cracks in a utility pole, a corroded wire-branch fitting, rust, etc. with a centimeter-order accuracy, through analysis of an image taken using MMS (Mobile Mapping System).

CITATION LIST

Non Patent Literature

[NPL 1] Kaneko and other two authors, "dejitaru kamera gazo wo mochiita konkurito no hibiware kensa gijyutsu", NTT Technical Journal, December 2011, pp. 21-24 (2011)

[NPL 2] Sasaki, "Akusesu setsubi unyo wo inobesyon suru gijyutsu kaihatsu", NTT Technology Journal, February 2017, pp. 51-55 (2017)

SUMMARY OF THE INVENTION

Technical Problem

However, with the conventional technologies, it is difficult to estimate the depth of each crack in a reinforced concrete structure based on visual information regarding the external appearance of the reinforced concrete structure. In other words, it is not possible to accurately determine whether or not each crack generated in the reinforced concrete structure reach a reinforcing steel bar. Therefore, there is a problem in that, even if a reinforcing steel bar is not actually corroded, the reinforced concrete structure is replaced or repaired, and the operating cost, maintenance cost, and so on are excessively spent.

An object of the present disclosure made in view of such circumstances is to provide an estimation method, an estimation device, and a program capable of estimating the depth of a crack generated in a reinforced concrete structure, based on information regarding the external appearance of the reinforced concrete structure.

Means for Solving the Problem

An estimation method according to an embodiment includes: an acquisition step of acquiring deflection stress information that indicates a relationship between a deflection and a tensile stress in a specimen of a reinforced concrete structure; and a derivation step of deriving an estimation formula for estimating a depth of a crack generated in the reinforced concrete structure when a deflection of the reinforced concrete structure is no less than a first deflection of the specimen at a start of a generation of the crack, and is no greater than a second deflection of the specimen at an end of the generation of the crack.

An estimation device according to an embodiment includes: an acquisition unit that acquires deflection stress information that indicates a relationship between a (deflection and a tensile stress in a specimen of a reinforced concrete structure; a derivation unit that derives an estimation formula for estimating a depth of a crack generated in the reinforced concrete structure when a deflection of the reinforced concrete structure is no less than a first deflection of the specimen at a start of a generation of the crack, and is no greater than a second deflection of the specimen at an end of the generation of the crack.

Also, to solve the above-described problem, a program according to the present invention enables a computer to function as the above-described estimation device.

Effects of the Invention

According to the present disclosure, it is possible to provide an estimation method, an estimation device, and a program capable of estimating the depth of a crack generated in a reinforced concrete structure, based on information regarding the external appearance of the reinforced concrete structure.

DESCRIPTION OF EMBODIMENTS

The following describes an embodiment in detail with reference to the drawings.

[Estimation Device]

First, an example of a configuration of an estimation device 100 according to the present embodiment will be described with reference to FIGS. 1 to 3.

Figure 1:
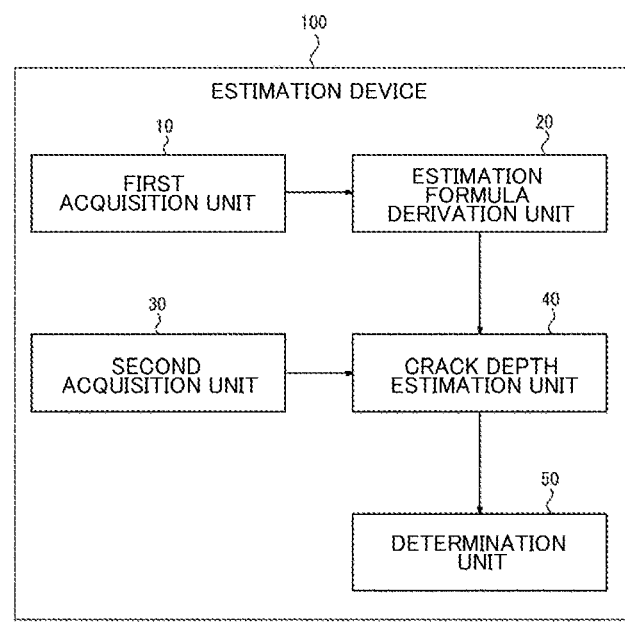
FIG. 1 is a diagram showing an example of a configuration of an estimation device according to the present embodiment.

As shown in FIG. 1, the estimation device 100 includes a first acquisition unit 10, an estimation formula derivation unit 20, a second acquisition unit 30, a crack depth estimation unit 40, and a determination unit 50.

An operator S (user) inputs a thickness D of a reinforced concrete structure to the estimation device 100 based on the specifications or the like of the reinforced concrete structure (actual structure). The first acquisition unit 10 acquires the thickness D of the reinforced concrete structure input by the user, and outputs the acquired thickness D of the reinforced concrete structure to the estimation formula derivation unit 20.

Also, the user inputs data indicating the deflection and the tensile stress in a specimen of the reinforced concrete structure (reinforced concrete specimen) to the estimation device 100. The reinforced concrete specimen is a specimen that has substantially the same specifications as the actual structure and is manufactured in order to perform the bending test described later. The reinforced concrete specimen is, for example, a concrete pole that has a length of 8000 mm, a bottom end diameter of 247 mm, a crack test load of 2.0 kN, and a taper of 1/75. The first acquisition unit 10 acquires the data input by the user, and generates and acquires deflection stress information that indicates the relationship between the deflection and the tensile stress of the reinforced concrete specimen. The user may use another device to generate deflection stress information and input the deflection stress information to the estimation device 100. In such a case, the first acquisition unit 10 acquires the deflection stress information input by the user. The first acquisition unit 10 outputs the acquired deflection stress information to the estimation formula derivation unit 20.

Figure 2:
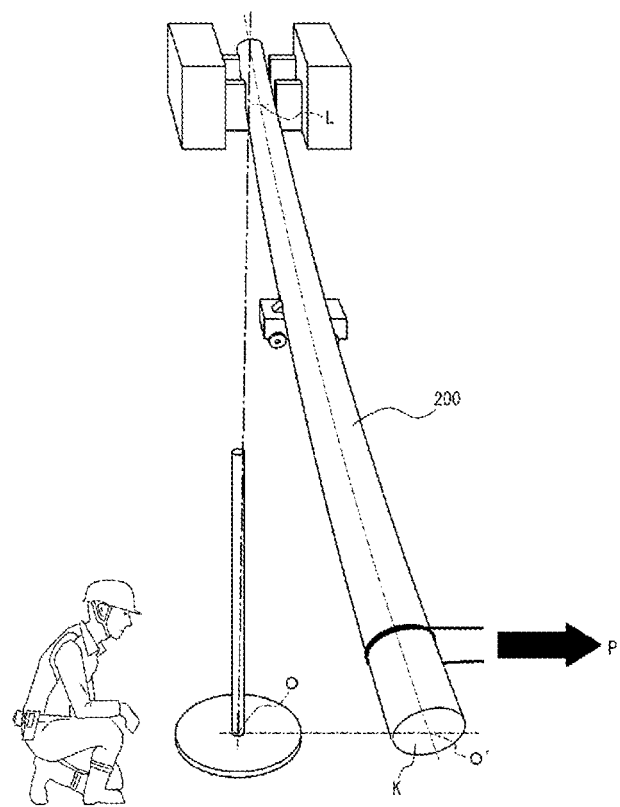
FIG. 2 is a diagram showing an example of a bending test according to the present embodiment.

For example, as shown in FIG. 2, the user obtains data that indicates the relationship between the deflection and the tensile stress through a bending test performed on a reinforced concrete specimen 200.

The reinforced concrete specimen 200 is supported by one fulcrum L, and bends when a load P is applied to the reinforced concrete specimen 200. That is to say, a leading K of the reinforced concrete specimen 200 is located at a point O in an unloaded state, but the leading end K moves so as to be located at a point O' in a state where a load P is applied. In the present description, the moving distance by which the leading end K of the reinforced concrete specimen 200 moves from the point O to the point O' is referred to as the deflection of the reinforced concrete specimen 200.

A strain gauge is attached to the reinforcing steel bars of the reinforced concrete specimen 200. While checking the strain of the reinforcing steel bar using the strain gauge, the user measures the deflection of the reinforced concrete specimen 200 and the tensile stress applied to the portion to which the strain gauge of the reinforced concrete specimen 200 is attached. Upon the user inputting various pieces of data such as the deflection of the reinforced concrete specimen 200 and the tensile stress of the reinforced concrete specimen 200 into a computer, and performing appropriate operations, the computer generates a graph (see FIG. 3) indicating the deflection stress information, using a graph creation application such as Microsoft Excel (registered trademark), and displays the generated graph on a display unit or the like.

Figure 3:
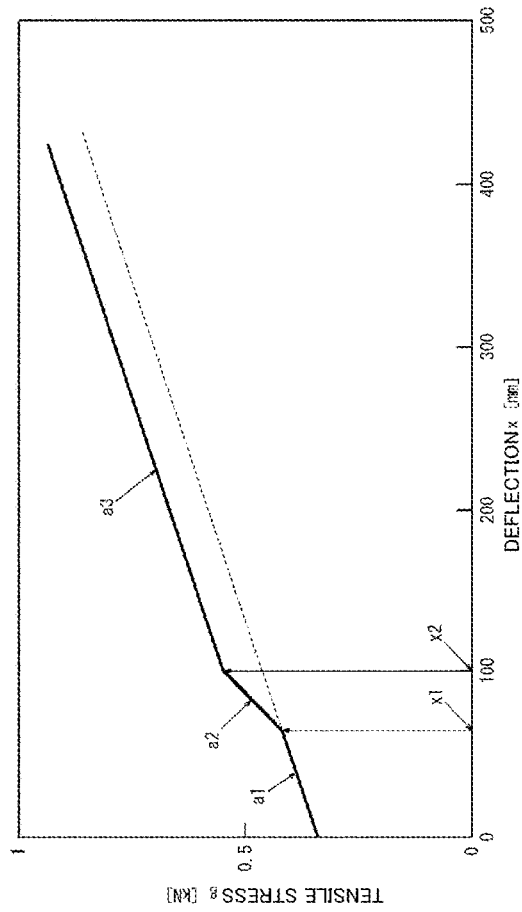
FIG. 3 is a diagram showing an example of deflection stress information indicating a relationship between a deflection and a tensile stress of a reinforced concrete specimen according to the present embodiment.

As shown in FIG. 3, the graph indicating the deflection stress information can be expressed by, for example, a formula $g=F(x)$. Generally, the graph can be approximated by a straight line in the interval of $x<x1$, the interval of $x1 \leq x \leq x2$, and the interval of $x2<x$. The slope of the graph corresponds to the elastic modulus of the reinforcing steel bar and is the constant of proportionality. The slope of the graph is expressed as the derivative of the formula $g=F(x)$. The rate of change of the slope of the graph is expressed as the second derivative of the formula $g=F(x)$.

The first acquisition unit 10 acquires the deflection of the reinforced concrete specimen 200 when the slope of the graph changes from a slope a1 to a slope a2, i.e., when the rate of change of the slope of the graph becomes positive, as a deflection x1 (first deflection) of the reinforced concrete specimen 200 at the start of the generation of a crack. The deflection x1 of the reinforced concrete specimen 200 at the start of the generation of a crack may be derived by the estimation formula derivation unit 20.

When the rate of change of the slope of the graph becomes positive, the slope of the graph increases and becomes steeper. At this time, the destruction of the concrete of the reinforced concrete specimen 200 is started, and the state of the reinforced concrete specimen 200 changes from the state where concrete and the reinforcing steel bars are subjected to the tensile stress to the state where the reinforcing steel bars are subjected to most of the tensile stress.

If a crack test load is set in the specifications of the reinforced concrete specimen 200, the first acquisition unit 10 may acquire the deflection of the reinforced concrete specimen 200 when the crack test load is applied thereto, as the deflection x1 of the reinforced concrete specimen 200 at the start of the generation of a crack.

The first acquisition unit 10 acquires the deflection of the reinforced concrete specimen 200 when the slope of the graph changes from the slope a2 to a slope a3, i.e., when the rate of change of the slope of the graph becomes negative, as a deflection x2 (second deflection) of the reinforced concrete specimen 200 at the end of the generation of a crack. The deflection x2 of the reinforced concrete specimen 200 at the end of the generation of a crack may be derived by the estimation formula derivation unit 20.

When the rate of change of the slope of the graph becomes negative, the slope of the graph decreases and becomes gentler. At this time, the progress of the destruction of the concrete of the reinforced concrete specimen 200 ends, and the crack generated in the reinforced concrete specimen 200 reaches the back surface of the concrete (the surface of a reinforcing steel bar), and the depth of the crack in the reinforced concrete specimen 200 matches the thickness of the concrete of the reinforced concrete specimen 200.

The estimation formula derivation unit 20 derives an estimation formula $d=f(x)$ for estimating the depth d of the crack in the reinforced concrete structure within a range defined by the condition described below, based on deflection stress information. Here, the condition is that the deflection x of the reinforced concrete structure acquired by the second acquisition unit 30 described later is no less than the deflection x1 of the reinforced concrete specimen 200 at the start of the generation of the crack, and is no greater than the deflection x2 of the reinforced concrete specimen 200 at the end of the generation of the crack ($x1 \leq x \leq x2$). The deflection of the reinforced concrete structure is a moving distance by which the leading end of the reinforced concrete structure moves when the reinforced concrete structure in a vertical state bends. The estimation formula derivation unit 20 outputs the derived estimation formula $d=f(x)$ to the crack depth estimation unit 40.

A proportional coefficient b of the crack in the reinforced concrete specimen 200 with respect to the deflection of the reinforced concrete specimen 200 is expressed by the following formula (1).

[Math. 1]

$$b = D/(x2 - x1) \quad (1)$$

If the deflection x of the reinforced concrete structure matches the deflection x1 of the reinforced concrete specimen 200 at the start of the generation of the crack, the depth d of the crack in the reinforced concrete structure is zero. If the deflection x of the reinforced concrete structure matches the deflection x2 of the reinforced concrete specimen 200 at the end of the generation of the crack, the depth d of the crack in the reinforced concrete structure is equal to the thickness D of the reinforced concrete structure. Therefore, the estimation formula d=f(x) when x satisfies x1≤x≤x2 is expressed by the following formula.

[Math. 2]

$$d = f(x) = b \times (x - x1) = D \times \{(x - x1)/(x2 - x1)\} \quad (2)$$

Note that, in the range of x1≤x≤x2 in the graph shown in FIG. 3, if the graph indicating deflection stress information does not have a proportional relationship, the estimation formula derivation unit 20 can also calculate a graph indicating deflection stress information through the least squares method or the like, and derive the estimation formula d=f(x) based on the result of the calculation.

The user inputs deflection information regarding the reinforced concrete structure, which can be obtained from the external appearance of the reinforced concrete structure, to the estimation device 100. The second acquisition unit 30 acquires the deflection information input by the user, and outputs the acquired deflection information to the crack depth estimation unit 40.

For example, the second acquisition unit 30 may acquire information regarding the deflection of the reinforced concrete structure based on visual confirmation performed by the user. Alternatively, for example, the second acquisition unit 30 may acquire information regarding the deflection of the reinforced concrete structure based on measurement data obtained through fixed point measurement performed by the user. Alternatively, for example, the second acquisition unit 30 may acquire information regarding the deflection of the reinforced concrete structure based on an image captured using an MMS.

Also, the second acquisition unit 30 acquires a cover thickness D' of the reinforced concrete structure based on the specifications or the like of the reinforced concrete structure. The cover thickness D' of the reinforced concrete structure is the shortest distance from the surfaces of the reinforcing steel bars of the reinforced concrete structure to the concrete surface of the reinforced concrete structure. The second acquisition unit 30 outputs the acquired cover thickness D' of the reinforced concrete structure to the estimation formula derivation unit 20.

The crack depth estimation unit 40 determines whether or not a crack has been generated in the reinforced concrete structure, and if a crack has been generated in the reinforced concrete structure, estimates the depth of the crack in the reinforced concrete structure. The crack depth estimation unit 40 outputs the estimated depth of the crack in the reinforced concrete structure to the determination unit 50.

For example, the crack depth estimation unit 40 determines that a crack has been generated in the reinforced concrete structure if the deflection of the reinforced concrete structure is no less than the deflection x1 of the reinforced concrete specimen 200 at the start of the generation of the crack. Also, for example, the crack depth estimation unit 40 determines that a crack has not been generated in the reinforced concrete structure if the deflection of the reinforced concrete structure is less than the deflection x1 of the reinforced concrete specimen 200 at the start of the generation of the crack. Alternatively, for example, if a crack test load is set in the specifications of the reinforced concrete specimen 200, the crack depth estimation unit 40 performs determination in the following manner. That is to say, the determination is to determine that a crack has been generated in the reinforced concrete structure if the deflection of the reinforced concrete structure is no less than the deflection when the crack test load is applied to the reinforced concrete specimen 200. Furthermore, the determination is to determine that a crack has not been generated in the reinforced concrete structure if the deflection of the reinforced concrete structure is less than the deflection when the crack test load is applied to the reinforced concrete specimen 200.

Upon determining that a crack has been generated in the reinforced concrete structure, the crack depth estimation unit 40 substitutes the deflection of the reinforced concrete structure for x in the above-described estimation formula d=f(x) to estimate the depth d of the crack in the reinforced concrete structure. Note that, upon determining that no crack has been generated in the reinforced concrete structure, the crack depth estimation unit 40 does not estimate the depth d of the crack in the reinforced concrete structure.

Based on the depth d of the crack in the reinforced concrete structure input from the crack depth estimation unit 40, the determination unit 50 compares the depth d of the crack in the reinforced concrete structure with the cover thickness D' of the reinforced concrete structure to determine whether or not the depth d of the crack in the reinforced concrete structure is no less than the cover thickness D' of the reinforced concrete structure.

If the depth d of the crack in the reinforced concrete structure is no less than the cover thickness D' of the reinforced concrete structure, the determination unit 50 determines that the crack generated in the reinforced concrete structure has reached a reinforcing steel bar of the reinforced concrete structure. If the depth d of the crack in the reinforced concrete structure is less than the cover thickness D' of the reinforced concrete structure, the determination unit 50 determines that the crack generated in the reinforced concrete structure has not reached a reinforcing steel bar of the reinforced concrete structure. The user can evaluate the health of the reinforced concrete structure by acquiring the result of the determination performed by the determination unit 50.

The estimation device 100 according to the present embodiment captures the process in which a crack develops, by grasping deflection stress information in advance, and derives an estimation formula for estimating the depth of the crack in the reinforced concrete structure. As a result, it possible to estimate the depth of a crack in the reinforced concrete structure based on information regarding the external appearance of the reinforced concrete structure.

In addition, the estimation device 100 according to the present embodiment accurately determines whether or not a crack generated in the reinforced concrete structure has reached a reinforcing steel bar of the reinforced concrete structure. As a result, it is possible to avoid the conventional problem in that reinforcing steel bars are considered to be exposed to a corrosive environment at the same time as a crack is generated, and the reinforced concrete structure is replaced or repaired even though the reinforcing steel bars are not actually corroded. That is to say, the reinforced concrete structure can be replaced or repaired only the crack generated in the reinforced concrete structure reaches a reinforcing bar of the reinforced concrete structure. Therefore, operating costs, maintenance costs, and so on can be reduced.

[Estimation Method]

Next, an example of an estimation method according to the present embodiment will be described with reference to FIG. 4.

In step S101, the first acquisition unit 10 acquires the thickness D of the reinforced concrete structure that is based on the specifications or the like of the reinforced concrete structure. Also, in step S101, the first acquisition unit 10 acquires deflection stress information that is based on the bending test performed on the reinforced concrete specimen 200.

In step S102, the estimation formula derivation unit 20 derives an estimation formula $d=f(x)$ for estimating the depth d of the crack in the reinforced concrete structure within the range of the conditions described below, based on the deflection stress information acquired in step S101. Here, the condition is that the deflection x of the reinforced concrete structure is no less than the deflection x1 of the reinforced concrete specimen 200 at the start of the generation of the crack, and is no greater than the deflection x2 of the reinforced concrete specimen 200 at the end of the generation of the crack.

In step S103, the second acquisition unit 30 acquires information regarding deflection of the reinforced concrete structure that is based on the external appearance of the reinforced concrete structure. Also, the second acquisition unit 30 acquires a cover thickness D' of the reinforced concrete structure that is based on the specifications or the like of the reinforced concrete structure.

In step S104, the crack depth estimation unit 40 determines whether or not a crack has been generated in the reinforced concrete structure. The crack depth estimation unit 40 determines that a crack has been generated in the reinforced concrete structure if the deflection of the reinforced concrete structure is no less than the deflection x1 of the reinforced concrete specimen 200 at the start of the generation of the crack, e.g., if the deflection of the reinforced concrete structure is no less than the deflection when a slope ratio a2/a1 in the graph shown in FIG. 3 is no less than 1.2. In this case, the crack depth estimation unit 40 proceeds to the processing in step S105. The crack depth estimation unit 40 determines that a crack has not been generated in the reinforced concrete structure if the deflection of the reinforced concrete structure is less than the deflection x1 of the reinforced concrete specimen 200 at the start of the generation of the crack, e.g., if the deflection of the reinforced concrete structure is less than the deflection when the slope ratio a2/a1 in the graph shown in FIG. 3 is less than 1.2. In this case, the crack depth estimation unit 40 terminates the processing.

In step S105, the crack depth estimation unit 40 estimates the depth d of the crack in the reinforced concrete structure based on the above-described estimation formula $d=f(x)$.

In step S106, the determination unit 50 compares the depth d of the crack in the reinforced concrete structure with the cover thickness D' of the reinforced concrete structure to determine whether or not the depth d of the crack in the reinforced concrete structure is no less than the cover thickness D' of the reinforced concrete structure. If the depth d of the crack in the reinforced concrete structure is no less than the cover thickness D' of the reinforced concrete structure ($d \geq D'$), the determination unit 50 proceeds to the processing in step S107. If the depth d of the crack in the reinforced concrete structure is less than the cover thickness D' of the reinforced concrete structure ($d < D'$), the determination unit 50 proceeds to the processing in step S108.

In step S107, the depth d of the crack in the reinforced concrete structure is no less than the cover thickness D' of the reinforced concrete structure, and therefore the determination unit 50 determines that the crack generated in the reinforced concrete structure has reached a reinforcing steel bar of the reinforced concrete structure.

In step S108, the depth d of the crack in the reinforced concrete structure is less than the cover thickness D' of the reinforced concrete structure, and therefore the determination unit 50 determines that the crack generated in the reinforced concrete structure has not reached a reinforcing steel bar of the reinforced concrete structure.

According to the above-described estimation method, by grasping deflection stress information in advance, the process in which a crack develops can be grasped, and an estimation formula for estimating the depth of the crack in the reinforced concrete structure can be derived. As a result, it possible to estimate the depth of a crack in the reinforced concrete structure based on information regarding the external appearance of the reinforced concrete structure.

In the present specification, a crack in the reinforced concrete structure refers to a crack generated in the concrete of the reinforced concrete structure, and a crack in the reinforced concrete specimen refers to a crack generated in the concrete of the reinforced concrete specimen.

<Program and Recording Medium>

It is also possible to use a computer capable of executing program instructions to function as the above embodiment. Such a computer can be realized by storing a program that describes the content of processing that realizes the functions of each device in a storage unit of the computer, and reading and executing this program, using a processor of the computer. At least a part of the content of such processing may be realized using hardware. Here, the computer may be a general-purpose computer, a dedicated computer, a workstation, a PC, an electronic notebook pad, or the like. The program instructions may be program codes, code segments, or the like that are used to execute required tasks. The processor may be a CPU (Central Processing Unit), a GPU (Graphics Processing Unit), a DSP (Digital Signal Processor), an ASIC (Application Specific Integrated Circuit), or the like.

Figure 4:
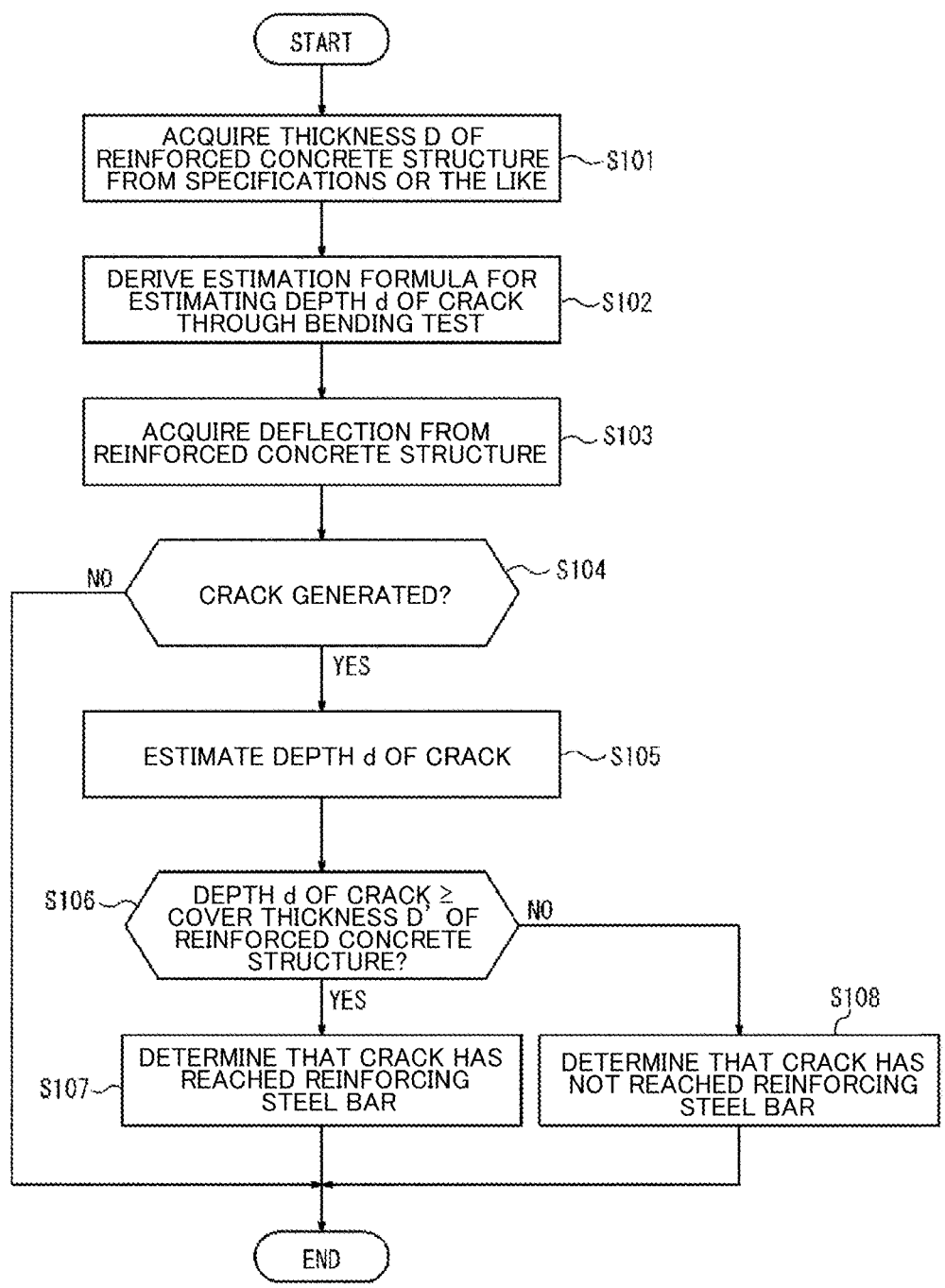
FIG. 4 is a flowchart showing an example of an estimation method according to the present embodiment.

For example, as shown in FIG. 4, a program that enables a computer to execute the above-described estimation method causes the computer to carry out an acquisition step S101 of acquiring deflection stress information, and a derivation step S102 of deriving an estimation formula for estimating a depth of a crack generated in a reinforced concrete structure when a deflection of the reinforced concrete structure is no less than a first deflection of a reinforced concrete specimen at a start of a generation of the crack, and is no greater than a second deflection of the reinforced concrete specimen at an end of the generation of the crack. In addition, the program may cause the computer to carry out a step S103 of acquiring information regarding deflection of the reinforced concrete structure, a step S104 of determining whether or not a crack has been generated in the reinforced concrete structure, a step S105 of estimating the depth d of the crack in the reinforced concrete structure, a step S106 of determining whether or not the depth d of the crack is no less than the cover thickness D' of the reinforced concrete structure, and steps S107 and S108 of determining whether or not the crack generated in the reinforced concrete structure has reached a reinforcing steel bar The program may also be recorded on a computer-readable recording medium. With such a recording medium, it is possible to install the program on a computer. Here, the recording medium on which the program is recorded may be a non-transitory recording medium. Such a non-transitory recording medium may be a CD (Compact Disk) -ROM (Read-Only Memory), DVD (Digital Versatile Disc) -ROM, BD (Blu-ray (registered trademark) Disc) -ROM, or the like. The program may also be provided by making it downloadable via a network.

Although the above embodiment has been described as representative examples, it will be apparent to those skilled in the art that many modifications and substitutions can be made within the spirit and scope of the present disclosure. Therefore, the present invention should not be construed as being limited by the embodiment described above, and various modifications and modifications can be made without departing from the scope of the claims. For example, it is possible to combine a plurality of constituent blocks described in the configuration diagram of the embodiment into one, or to divide one constituent block. Also, it is possible to combine a plurality of steps described in the flowchart of the embodiment into one, or to divide one step.

REFERENCE SIGNS LIST

10 First Acquisition Unit (Acquisition Unit)
20 Estimation Formula Derivation Unit
30 Second Acquisition Unit
40 Crack Depth Estimation Unit
50 Determination Unit
100 Estimation Device
200 Reinforced Concrete Specimen

The invention claimed is:

1. An estimation method, performed by an estimation device, the estimation method comprising:
   determining, based on measuring a reinforced concrete structure, thickness data of the reinforced concrete structure, wherein the reinforced concrete structure includes a reinforced concrete material;
   acquiring deflection stress data of a specimen of the reinforced concrete material by measuring deflections while applying tensile stresses and bending the specimen of the reinforced concrete material, wherein the deflection stress data indicate a relationship between a deflection and a tensile stress of the specimen of the reinforced concrete material;
   determining, based on the deflection stress data, a first deflection of the specimen at a first tensile stress and a second deflection of the specimen at a second tensile stress, wherein the first deflection of the specimen represent a beginning of generating a crack on the specimen, and the second deflection of the specimen represent an end of generating the crack on the specimen;
   acquiring, based on image data of an external appearance of the reinforced concrete structure, deflection information of the reinforced concrete structure;
   determining, based at least on the first second deflections of the specimen and the acquired deflection information of the reinforced concrete structure, a set of operations for estimating a depth of a crack being generated in the reinforced concrete structure, wherein a deflection of the reinforced concrete structure is no less than the first deflection of the specimen, and the deflection information of the reinforced concrete structure is no greater than a second deflection of the specimen at an end of the generation of the crack, and the set of operations indicates an estimation formula for the depth of the crack;
   determining, based on the determined set of operations for estimating the crack being generated in the reinforced concrete structure, depth information of the crack in the reinforced concrete structure, wherein the depth information indicates an estimated depth of the crack being generated in the reinforced concrete structure; and
   transmitting the depth information to an application configured to output an estimation of the crack being generated in the reinforced concrete structure.

2. The estimation method according to claim 1, further comprising:
   in response to determination that the crack has been generated in the reinforced concrete structure, estimating the depth of the crack based on the estimation formula;
   determining that the crack has reached a reinforcing steel bar of the reinforced concrete structure if the depth of the crack is no less than a cover thickness of the reinforced concrete structure; and
   determining that the crack has not reached the reinforcing steel bar of the reinforced concrete structure if the depth of the crack is less than the cover thickness of the reinforced concrete structure.

3. The estimation method according to claim 2,
wherein the determining the depth information of the crack further includes determining the crack having been generated when the deflection information of the reinforced concrete structure obtained from an external appearance no less than the first deflection.

4. The estimation method according to claim 2,
wherein the determining the set of operations further includes determining the estimation formula based on a rate of change of a slope of a graph indicating the deflection stress information obtained through a bending test performed on the specimen.

5. The estimation method according to claim 2,
wherein the estimation formula includes:

$$d = D \times \{(x-x1)/(x2-x1)\},$$

where D denotes the thickness of the reinforced concrete structure, x denotes the deflection information of the reinforced concrete structure, x1 denotes the first deflection, x2 denotes the second deflection, and d denotes the depth of the crack in the reinforced concrete structure.

6. The estimation method according to claim 1,
wherein the determining the set of operations further includes determining the estimation formula based on a rate of change of a slope of a graph indicating the deflection stress data obtained through a bending test performed on the specimen.

7. The estimation method according to claim 1,
wherein the estimation formula includes:

$$d = D \times \{(x-x1)/(x2-x1)\},$$

where D denotes the thickness of the reinforced concrete structure, x denotes the deflection information of the reinforced concrete structure, x1 denotes the first deflection, x2 denotes the second deflection, and d denotes the depth of the crack in the reinforced concrete structure.

8. An estimation device comprising a processor configured to execute operations comprising:
  determining, based on measuring a reinforced concrete structure, thickness data of the reinforced concrete structure, wherein the reinforced concrete structure includes a reinforced concrete material;
  acquiring deflection stress data of a specimen of the reinforced concrete material by measuring deflections while applying tensile stresses and bending the specimen of the reinforced concrete material, wherein the deflection stress data indicate a relationship between a deflection and a tensile stress of the specimen of the reinforced concrete material;
  determining, based on the deflection stress data, a first deflection of the specimen at a first tensile stress and a second deflection of the specimen at a second tensile stress, wherein the first deflection of the specimen represent a beginning of generating a crack on the specimen, and the second deflection of the specimen represent an end of generating the crack on the specimen;
  acquiring, based on image data of an external appearance of the reinforced concrete structure, deflection information of the reinforced concrete structure;
  determining, based at least on the first second deflections of the specimen and the acquired deflection of the reinforced concrete structure, a set of operations for estimating a depth of a crack being generated in the reinforced concrete structure, wherein a deflection of the reinforced concrete structure is no less than the first deflection of the specimen, and the deflection information of the reinforced concrete structure is no greater than a second deflection of the specimen at an end of the generation of the crack, and the set of operations indicates an estimation formula for the depth of the crack;
  determining, based on the determined set of operations for estimating the crack being generated in the reinforced concrete structure, depth information of the crack in the reinforced concrete structure, wherein the depth information indicates an estimated depth of the crack being generated in the reinforced concrete structure; and
  transmitting the depth information to an application configured to output an estimation of the crack being generated in the reinforced concrete structure.

9. The estimation device according to claim 8, the processor further configured to execute a method comprising:
  in response to determination that the crack has been generated in the reinforced concrete structure, estimating the depth of the crack based on the estimation formula;
  determining that the crack has reached the reinforcing steel bar of the reinforced concrete structure if the depth of the crack is no less than a cover thickness of the reinforced concrete structure; and
  determining that the crack has not reached a reinforcing steel bar of the reinforced concrete structure if the depth of the crack is less than the cover thickness of the reinforced concrete structure.

10. The estimation device according to claim 9, wherein the determining the depth information of the crack further includes determining the crack having been generated when the deflection information of the reinforced concrete structure obtained from an external appearance is no less than the first deflection.

11. The estimation device according to claim 9, wherein the determining the set of operations further includes determining the estimation formula based on a rate of change of a slope of a graph indicating the deflection stress information obtained through a bending test performed on the specimen.

12. The estimation device according to claim 9, wherein the estimation formula includes:

$$d = D \times \{(x-x1)/(x2-x1)\},$$

where D denotes the thickness of the reinforced concrete structure, x denotes the deflection information of the reinforced concrete structure, x1 denotes the first deflection, x2 denotes the second deflection, and d denotes the depth of the crack in the reinforced concrete structure.

13. The estimation device according to claim 8,
wherein the determining the set of operations further includes determining the estimation formula based on a rate of change of a slope of a graph indicating the deflection stress information obtained through a bending test performed on the specimen.

14. The estimation device according to claim 8,
wherein the estimation formula includes:

$$d = D \times \{(x-x1)/(x2-x1)\},$$

where D denotes the thickness of the reinforced concrete structure, x denotes the deflection information of the reinforced concrete structure, x1 denotes the first deflection, x2 denotes the second deflection, and d denotes the depth of the crack in the reinforced concrete structure.

15. A computer-readable non-transitory recording medium storing computer-executable program instructions that when executed by a processor cause a computer to execute operations comprising:
  determining, based on measuring a reinforced concrete structure, thickness data of the reinforced concrete structure, wherein the reinforced concrete structure includes a reinforced concrete material;
  acquiring deflection stress data of a specimen of the reinforced concrete material by measuring deflections while applying tensile stresses and bending the specimen of the reinforced concrete material, wherein the deflection stress data indicate a relationship between a deflection and a tensile stress of the specimen of the reinforced concrete material;
  determining, based on the deflection stress data, a first deflection of the specimen at a first tensile stress and a second deflection of the specimen at a second tensile stress, wherein the first deflection of the specimen represent a beginning of generating a crack on the specimen, and the second deflection of the specimen represent an end of generating the crack on the specimen;
  acquiring, based on image data of an external appearance of the reinforced concrete structure, deflection information of the reinforced concrete structure;
  determining, based at least on the first second deflections of the specimen and the acquired deflection of the reinforced concrete structure, a set of operations for estimating a depth of a crack being generated in the reinforced concrete structure, wherein a deflection of the reinforced concrete structure is no less than the first deflection of the specimen and the deflection information of the reinforced concrete structure is no greater than a second deflection of the specimen at an end of the generation of the crack, and the set of operations indicates an estimation formula for the depth of the crack;

determining, based on the determined set of operations for estimating the crack being generated in the reinforced concrete structure, depth information of the crack in the reinforced concrete structure, wherein the depth information indicates an estimated depth of the crack being generated in the reinforced concrete structure; and transmitting the depth information to an application configured to output an estimation of the crack being generated in the reinforced concrete structure.

16. The computer-readable non-transitory recording medium according to claim 15, the computer-executable program instructions further cause a computer to execute operations comprising:

in response to determination that the crack has been generated in the reinforced concrete structure, estimating the depth of the crack based on the estimation formula;

determining that the crack has reached a reinforcing steel bar of the reinforced concrete structure if the depth of the crack is no less than a cover thickness of the reinforced concrete structure; and determining that the crack has not reached the reinforcing steel bar of the reinforced concrete structure if the depth of the crack is less than the cover thickness of the reinforced concrete structure.

17. The computer-readable non-transitory recording medium according to claim 16, wherein the determining the depth information of the crack further includes determining the crack having been generated when the deflection information of the reinforced concrete structure obtained from an external appearance no less than the first deflection.

18. The computer-readable non-transitory recording medium according to claim 16, wherein the determining the set of operations further includes determining the estimation formula based on a rate of change of a slope of a graph indicating the deflection stress information obtained through a bending test performed on the specimen.

19. The computer-readable non-transitory recording medium according to claim 15, wherein the determining the set of operations further includes determining the estimation formula based on a rate of change of a slope of a graph indicating the deflection stress information obtained through a bending test performed on the specimen.

20. The computer-readable non-transitory recording medium according to claim 15, wherein the estimation formula includes:

$$d = D \times \{(x-x1)/(x2-x1)\},$$

where D denotes the thickness of the reinforced concrete structure, x denotes the deflection information of the reinforced concrete structure, x1 denotes the first deflection, x2 denotes the second deflection, and d denotes the depth of the crack in the reinforced concrete structure.

* * * * *